United States Patent
Shi et al.

(10) Patent No.: US 9,743,646 B2
(45) Date of Patent: Aug. 29, 2017

(54) METHOD OF ESTABLISHING ISOGENIC MULTI-XENOGRAFT MODEL AND THE USE THEREOF

(71) Applicant: Crown Bioscience Inc. (Taicang), Taicang (CN)

(72) Inventors: Qian Shi, Taicang (CN); Yanmei Sun, Taicang (CN)

(73) Assignee: CROWN BIOSCIENCE INC. (TAICANG), Taicang (CN)

( * ) Notice: Subject to any disclaimer, the term of this patent is extended or adjusted under 35 U.S.C. 154(b) by 0 days.

(21) Appl. No.: 14/679,924

(22) Filed: Apr. 6, 2015

(65) Prior Publication Data

US 2015/0282459 A1    Oct. 8, 2015

(30) Foreign Application Priority Data

Apr. 4, 2014  (CN) .......................... 2014 1 0135394

(51) Int. Cl.
| | | |
|---|---|---|
| *A01K 67/027* | (2006.01) | |
| *A61K 48/00* | (2006.01) | |
| *A61K 49/00* | (2006.01) | |

(52) U.S. Cl.
CPC ...... *A01K 67/0271* (2013.01); *A61K 49/0008* (2013.01); *A01K 2207/12* (2013.01); *A01K 2227/105* (2013.01); *A01K 2267/0331* (2013.01)

(58) Field of Classification Search
None
See application file for complete search history.

(56) References Cited

PUBLICATIONS

Torrance et al., Nat Biotech 2001, 19:940.*
Ni et al., Cancer Discovery 2012, 2:425.*

* cited by examiner

*Primary Examiner* — Doug Schultz
(74) *Attorney, Agent, or Firm* — Jun He Law Offices P.C.; James J. Zhu

(57) ABSTRACT

The present invention provides an immuno-deficient animal useful as an animal model for a human disease associated with a first mutation of a target gene, wherein the animal comprises (a) a first human xenograft comprising the target gene comprising the first mutation; (b) a second human xenograft comprising the target gene but lacking the first mutation, wherein the first human xenograft and second human xenograft are isogenic. Also provided here are methods of producing the animal model and methods of using such animal model.

10 Claims, 6 Drawing Sheets

METHOD OF ESTABLISHING ISOGENIC MULTI-XENOGRAFT MODEL AND THE USE THEREOF

RELATED APPLICATIONS

This application relates to and claims priority benefits from CN Patent Application No. 201410135394.1, filed Apr. 4, 2014, entitled "Method of establishing Isogenic multi-Xenograft model and the use thereof", which is hereby incorporated by reference by its entirety.

FIELD OF THE INVENTION

The present disclosure generally relates to an animal model for human disease, methods of producing the animal model and methods of using such animal model.

BACKGROUND OF THE INVENTION

Basic medical researches especially those in the field of active drug screening and pre-clinical drug tests are often carried out in animal models (eg. using rodents). Mutations of a single gene can lead to missing or malformed proteins, and in many cases may cause various diseases such as Malaria, AIDS, cancer etc. with different severity, of different sub-type, or at different stages and thus resulting different responsiveness to a particular therapeutic agent or treatment. It is then desirable to establish an effective platform in the drug discovery process to evaluate and profile different responsiveness of various gene mutations to a particular therapeutic agent or treatment.

Personalized healthcare, with which medical decisions, practices, and/or products are tailored to the individual patient, has become a very popular medical concept nowadays. However, there still exist great needs to personalize the treatments to different patients.

BRIEF SUMMARY OF THE INVENTION

The present disclosure provides animal models for a human disease, methods of producing the animal models and methods of using such animal models.

In one aspect, present disclosure provides an immuno-deficient animal useful as an animal model for a human disease associated with a first mutation of a target gene, wherein the animal comprises (a) a first human xenograft comprising the target gene comprising the first mutation; (b) a second human xenograft comprising the target gene but lacking the first mutation, wherein the first human xenograft and second human xenograft are isogenic. In some embodiments, the first human xenograft and the second human xenograft are grafted to different sites of the animal.

In some embodiments, the disease is cancer. In some embodiments, the target gene is selected from the group consisting of PI3K, EGFR, p53, RAS, N-RAS, K-RAS, B-RAF, C-KIT, PDGFRA, BCR-ABL and JAK2K. In certain embodiments, the target gene is K-RAS. In some embodiments, the first mutation is selected from the group consisting of G12C, G12R, G12S, G12V, G12D, G12A, G13V/D.

In some embodiments, the animal is a mammal. In some embodiments, the mammal is a rodent. In some embodiments, the rodent is a mouse, a rat, a guinea pig, a hamster.

In another aspect, the present disclosure provides method for producing an animal model for a human disease associated with a first mutation of a target gene, comprising: obtaining an immuno-deficient animal; and grafting the animal at a first site with a first human xenograft comprising the target gene comprising the first mutation, and at a second site with a second human xenograft comprising the target gene but lacking the first mutation, wherein the first human xenograft and second human xenograft are isogenic. In some embodiments, the first site and the second site are different. In some embodiments, the first human xenograft and/or the second human xenograft are grafted subcutaneously, intravenously, or intraperitoneally.

In some embodiments, the method for producing an animal model for a human disease associated with a first mutation of a target gene further comprises allowing the first and the second human xenografts to grow for a time sufficient to simulate the lesion of the human disease.

In some embodiments, the disease is cancer. In some embodiments, the target gene is selected from the group consisting of PI3K, EGFR, p53, RAS, N-RAS, K-RAS, B-RAF, C-KIT, PDGFRA, BCR-ABL and JAK2K. In certain embodiments, the target gene is K-RAS. In some embodiments, the first mutation is selected from the group consisting of G12C, G12R, G12S, G12V, G12D, G12A, G13V/D.

In some embodiments, the animal is a mammal. In some embodiments, the mammal is a rodent. In some embodiments, the rodent is a mouse, a rat, a guinea pig, a hamster.

In a third aspect, the present disclosure provides a method of assessing effect of a test agent on a human disease associated with a first mutation of a target gene, comprising: (a) obtaining an animal provided herein for the human disease; (b) administering the test agent to the animal; (c) determining the effect of the test agent on the first and the second human xenografts, respectively; and (d) comparing the effects of the test agent on the first and the second human xenografts. In some embodiments, the human disease is cancer. In some embodiments, the test agent is an active agent for cancer therapy.

In some embodiments, the disease is cancer. In some embodiments, the target gene is selected from the group consisting of PI3K, EGFR, p53, RAS, N-RAS, K-RAS, B-RAF, C-KIT, PDGFRA, BCR-ABL and JAK2K. In certain embodiments, the target gene is K-RAS. In some embodiments, the first mutation is selected from the group consisting of G12C, G12R, G12S, G12V, G12D, G12A, G13V/D.

In some embodiments, the animal is a mammal. In some embodiments, the mammal is a rodent. In some embodiments, the rodent is a mouse, a rat, a guinea pig, a hamster.

In a fourth aspect, the present disclosure provides methods of profiling effects of a test agent on a human disease associated with different mutations of a target gene, comprising: (a) obtaining a first animal provided herein for the human disease associated with a first mutation of the target gene; (b) administering the test agent to the first animal; (c) determining the effect of the test agent on the first and the second human xenografts respectively of the first animal; (d) obtaining a second animal provided herein for the human disease associated with a second mutation of the target gene; (e) administering the test agent to the second animal; (f) determining the effect of the test agent on the first and the second human xenografts respectively of the second animal; and (g) recording the effects of the test agent on the first animal and the second animal respectively.

In some embodiments, the disease is cancer. In some embodiments, the target gene is selected from the group consisting of PI3K, EGFR, p53, RAS, N-RAS, K-RAS, B-RAF, C-KIT, PDGFRA, BCR-ABL and JAK2K. In certain embodiments, the target gene is K-RAS. In some embodiments, the first mutation is selected from the group consisting of G12C, G12R, G12S, G12V, G12D, G12A, G13V/D.

In some embodiments, the animal is a mammal. In some embodiments, the mammal is a rodent. In some embodiments, the rodent is a mouse, a rat, a guinea pig, a hamster.

In a fifth aspect, present disclosure provides methods of identifying an active agent effective on a human disease associated with a first mutation of a target gene, comprising: (a) obtaining the animal provided herein for the human disease; (b) administering a test agent to the animal; (c) determining the effect of the test agent on the first and the second human xenografts, respectively of the animal; wherein therapeutic improvement in the first human xenograft indicates the test agent is an active agent.

In some embodiments, the disease is cancer. In some embodiments, the target gene is selected from the group consisting of PI3K, EGFR, p53, RAS, N-RAS, K-RAS, B-RAF, C-KIT, PDGFRA, BCR-ABL and JAK2K. In certain embodiments, the target gene is K-RAS. In some embodiments, the first mutation is selected from the group consisting of G12C, G12R, G12S, G12V, G12D, G12A, G13V/D.

In some embodiments, the animal is a mammal. In some embodiments, the mammal is a rodent. In some embodiments, the rodent is a mouse, a rat, a guinea pig, a hamster.

In a sixth aspect, the present disclosure provides methods of predicting effect of a test agent on a patient having a disease associated with a first mutation of a target gene, comprising: (a) obtaining the animal provided herein for the disease, wherein the first human xenograft comprising the target gene comprising the first mutation is obtained from one individual, and the second human xenograft comprising the target gene but lacking the first mutation is obtained from another individual; (b) administering the test agent to the animal; and (c) determining the effect of the test agent on the first and the second human xenografts, respectively of the animal, wherein therapeutic improvement in the first human xenograft indicates efficacy of the test agent.

In some embodiments, the disease is cancer. In some embodiments, the target gene is selected from the group consisting of PI3K, EGFR, p53, RAS, N-RAS, K-RAS, B-RAF, C-KIT, PDGFRA, BCR-ABL and JAK2K. In certain embodiments, the target gene is K-RAS. In some embodiments, the first mutation is selected from the group consisting of G12C, G12R, G12S, G12V, G12D, G12A, G13V/D.

In some embodiments, the animal is a mammal. In some embodiments, the mammal is a rodent. In some embodiments, the rodent is a mouse, a rat, a guinea pig, a hamster.

DETAILED DESCRIPTION OF THE INVENTION

Figure 1A:
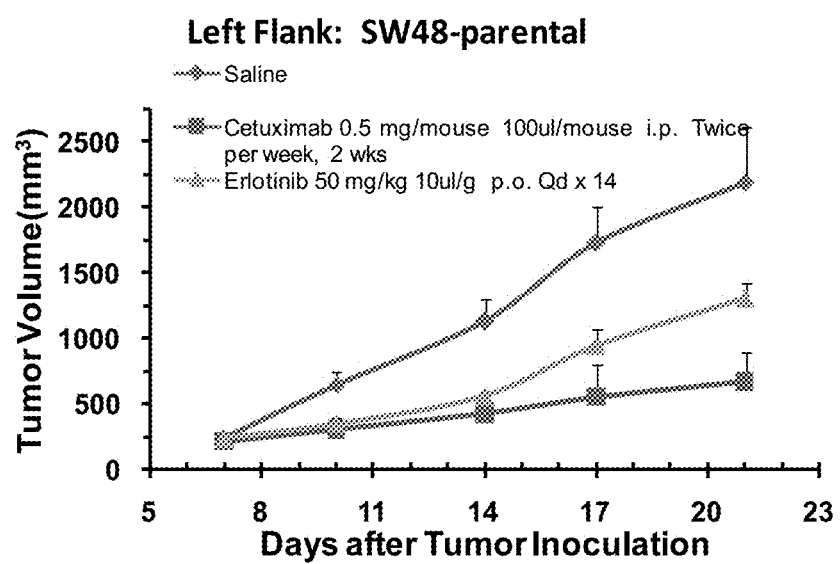
FIG. 1A. Antitumor activity of Control agent (Saline), Cetuximab, and Erlotinib (n=5/group) in the treatment of SW48-parental and SW48-KRAS (G13D/+) Isogenic Dual Xeno models. The data show the tumor volume of SW48-parental xenograft in the models. Each data point represents an average of data from 5 individual mice, error bars represent SEM.

The present disclosure provides animal models for a human disease, methods of producing the animal models and methods of using such animal models.

The animal models provided herein are grafted with a pair of isogenic human xenografts, both of which share the same target gene except that one has a mutation of interest while the other has not. This allows direct comparison or study of the two specific genetic variances within the same animal. The isogenic animal models provided herein can also allow predication of how a patient with a specific genetic background would respond to various therapeutic agents or treatments, and such predication can provide guidance for selecting appropriate and optimal therapies for the patient based on the context of his own genetic profile.

The human xenograft comprises a disease cell or tissue, which, after being grafted to the animal, can simulate or mimic the human disease or a lesion of the disease. The disease can be associated with the mutation of interest of the target gene. In particular, presence and absence of the mutation can lead to difference in the disease, for example, different severity of the disease, different subtypes of the disease, different stage of the disease, different responsiveness to a particular therapeutic agent, and so on. As such, the animal models provided herein are particularly useful in comparing or evaluating genetic variants of a human disease, and also in evaluating responsiveness of the genetic variants to a particular therapeutic agent.

Animal Model

One aspect of the present disclosure provides an immunodeficient animal useful as an animal model for a human disease associated with a first mutation of a target gene, comprises (a) a first human xenograft comprising the target gene comprising the first mutation; (b) a second human xenograft comprising the target gene but lacking the first mutation, wherein the first human xenograft and second human xenograft are isogenic.

The term "animal" as used herein refers to all vertebrate animals except human, preferably a mammal, such as a dog, a pig, a rabbit, or a rodent (eg. a mouse, a rat, a hamster, a guinea pig or such like). In certain embodiments, the animal is a mammal. In certain embodiments, the animal is a rodent. In certain embodiments, the animal is a mouse, a rat, a guinea pig, a hamster, a dog, or a monkey.

The term "animal model" as used herein refers to any non-human animals directly or indirectly manipulated (eg. genetically modified, or grafted with cells or tissue) to include one or more cells bearing altered or exogenous genetic information. In a particular aspect of this invention, the animal model is an immuno-compromised non-human animal capable of receiving and supporting a xenograft without mounting a graft-rejection immune response. An "immuno-compromised" animal can either be an immuno-deficient animal which is genetically deprived of endogenous T cells, B cells, NK cells or a combination thereof. Alternatively, an animal can be immuno-suppressed by biological or chemical means. Such biological or chemical means include, without limitation, immuno-suppression by repeated treatment with irradiation, cyclosporine, anti-Asialo GM1 antibody, or other immuno-suppressive agents or treatments well known in the art.

In some of the embodiments, the animal model of present disclosure is immuno-deficient. The term "immuno-deficient" is used herein to describe the animal in which the immune system has been partly or completely compromised, such that it does not generate sufficient immune response to reject a foreign graft (such as a foreign cell or a tissue) and therefore is capable of accepting and supporting the foreign graft as self. Examples of immuno-deficient animals include, for example: T lymphocytes deficient animals (eg. BALB/c nude mice, C57BL nude mice, NIH nude mice, nude rat, etc.); B lymphocytes deficient animals (eg. CBA/N mice); NK cell deficient animal (eg. Beige mice); combined immuno-deficient animal (eg. severe combined immuno-deficient (SCID) mice (combined T and B lymphocytes deficient), Beige/Nude (combined T lymphocytes and NK cells deficient), SCID Beige/SCID NOD mice (combined T, B lymphocytes and NK cells deficient)) and such like.

The animal models provided herein simulate or mimic a human disease associated with a first mutation of a target gene. In certain embodiments, the human disease is a proliferative disease which involves uncontrolled cell growth. In certain embodiments, the human disease is tumor or cancer.

As used herein, a human disease "associated with" a mutation means that presence and absence of the mutation in the target gene could render pathological difference in the disease, for example, difference in severity of the disease, subtypes of the disease, stages of the disease, responsiveness to a particular therapeutic agent, and the like.

"Mutation" as used herein includes substitution, deletion, and/or insertion of one or more nucleotides. For example, mutation can be a point mutation where one nucleotide is substituted for another nucleotide, a deletion where one or more nucleotides is deleted from the target gene, an insertion where one or more nucleotide from another nucleotide sequence is inserted into the target gene, a fusion where a fragment of the target gene is fused to at least a fragment of another gene or another nucleotide sequence, or any combination of the above.

"Target gene" as used herein refers to a gene of interest. In certain embodiments, the target gene is selected from the group consisting of PI3K (NCBI GENE BANK ACCESSION NUMBER: 5290), EGFR (NCBI GENE BANK ACCESSION NUMBER: 1956), p53 (NCBI GENE BANK ACCESSION NUMBER: 7157), RAS eg. N-RAS (NCBI GENE BANK ACCESSION NUMBER: 4893) or K-RAS (NCBI GENE BANK ACCESSION NUMBER: 3845), B-RAF (NCBI GENE BANK ACCESSION NUMBER: 673), C-KIT (NCBI GENE BANK ACCESSION NUMBER: 3815), PDGFRA (NCBI GENE BANK ACCESSION NUMBER: 5156), BCR-ABL (NCBI GENE BANK ACCESSION NUMBER: 613) and JAK2K (NCBI GENE BANK ACCESSION NUMBER: 3717). In certain embodiments, mutations of these target genes are associated with tumor or cancer. In certain embodiments, the target gene is K-RAS. Mutations of K-RAS are associated with human tumor or cancer. In certain embodiments, the mutation of K-RAS is selected from the group consisting of G12C, G12R, G12S, G12V, G12D, G12A, G13V/D.

The animal models provided herein comprise a first human xenograft and a second human xenograft.

The term "xenograft" as used herein refers to a graft of tissue or cells taken from a donor which is a species different from the animal model, and grafted into the animal model. In some embodiments, the donor of the xenograft is human. In some embodiments, the xenograft tissue or cells are tumor tissue or cells, or cancerous tissue or cells. In some embodiments, the xenograft is pre-treated before grafting into the animal model. The term "pre-treated" when refers to tissue, generally relates to any processing methods known in the art to treat a tissue before its engraftment, such as washing, homogenization, re-suspension and mixing with a solution (eg. saline, PBS etc.) or a matrix (eg. collagen). The term "pre-treated" when refers to cells, includes any processing methods known in the art to treat cells before its engraftment, such as culture, sub-culture, activating, treatment with an agent, centrifugation, re-suspension, filtration, and mixing with a solution (eg. saline, PBS etc.) or a matrix (eg. collagen). After grafted with xenograft, the animal model is allowed sufficient time to develop a lesion of the human disease for further use.

The xenograft can be grafted to the animal model using any suitable methods known in the art, for example, by grafting cells subcutaneously, intraperitoneally, or intravenously through injection; or alternatively, by implanting a fraction of tissue through surgery. In some embodiments, the xenografts are tumor cells or cancerous cells, and are grafted to the animal model through subcutaneously injection.

The first human xenograft and the second human xenograft are grafted to different sites of the animal model. The site of implantation may be into any subcutaneous site which will permit blood supply to reach the implant, such as the flanks of the host animal. For example, the first and the second xenografts are grafted respectively to the left and the right flanks of the animal.

The first human xenograft and the second human xenograft are isogenic except that the first human xenograft comprises the target gene comprising the first mutation of interest, whereas the second human xenograft comprises the target gene lacking the first mutation of interest.

The term "isogenic" when used with respect to the xenografts, means the first and the second xenografts both share the same genetic background and have the same target gene although they differ in certain mutation(s) in the target gene.

In certain embodiments, the first and the second isogenic xenografts are derived from the same origin (e.g. the same cell line, the same subject, etc., and therefore share the same genetic background), but one of the xenografts is further modified to introduce the mutation of interest, or to remove the mutation of interest. Suitable methods such as gene editing techniques can be used to modify the xenograft to introduce or remove the mutation of interest, for example, without limitation, methods using Adeno-Associated Virus (AAV) homologous recombination vectors, Zinc Finger Nuclease (ZFN) genome editing methods, and/or CRISPR-Cas9 genome editing methods. For example, suppose the cell line or the subject has the mutation of interest in the target gene, and two cell samples or tissue samples derived from the cell line or the subject are obtained, in which one sample is grafted to the animal model as the first xenograft comprising the mutation, and the other is modified to remove the mutation without changing the remaining genetic background and then grafted to the animal model as the second xenograft lacking the mutation. For another example, suppose the subject does not have the mutation of interest in the target gene, and two cell samples or tissue samples derived from the cell line or the subject are obtained, in which one is modified to introduce the mutation without changing the remaining genetic background and then grafted to the animal model as the first xenograft comprising the mutation, and the other is grafted without any modification to the animal model as the second xenograft lacking the mutation.

Isogenic xenografts in the same animal model allow definitive study or comparison of specific genetic variances, and provide an excellent tool for evaluating therapeutic responses of different gene mutations.

In certain embodiments, the second xenograft is isogenic to the first xenograft but lacks the first mutation in the target gene. In certain embodiment, the second xenograft is wild type at the site of the first mutation. For example, the first xenograft comprises G12C in the target gene K-RAS, whereas the second xenograft comprises G at the $12^{th}$ amino acid, which is the wild type nucleotide. In certain embodiment, the second xenograft comprises a different mutation at the site of the first mutation, thereby "lacking" the first mutation. For example, the first xenograft comprises G12C in the target gene K-RAS, whereas the second xenograft comprises G12R, which is a different mutation and is not wild type but nevertheless lacks the mutation of G12C in the first xenograft.

In certain embodiments, the animal model further comprises a third human xenograft comprising the target gene which lacks the first mutation but comprises a second mutation. For example, at the site (e.g. the $12^{th}$ amino acid of K-RAS) of the first mutation of the target gene, the second xenograft may be wild type (e.g. having a G12), the first xenograft comprises the first mutation (e.g. having a G12C), and the third xenograph may comprises a second mutation (e.g. having a G12R) which is different from the first mutation. For another example, at the site (e.g. the $12^{th}$ amino acid of K-RAS) of the first mutation of the target gene, the first xenograft comprises the first mutation (e.g. having a G12C), the second xenograft may comprise the second mutation (e.g. having a G12R), and the third xenograph may comprises a third mutation (e.g. having a G12S), and both of the second and the third mutations are different from the first mutation.

The animal model described above can be used to test or select candidate drug or compound for efficacy on disease development and progression, or to test the efficacy of a conventional drug for a disease in the treatment of individuals with specific mutations of gene. In some embodiments, the test or selection are carried out in samples or specimens (e.g., blood, a biopsy) from the animals. In some embodiments, the test or selection are carried out by observing the physical changes (e.g. weight loss/gain, size of disease related lesion) of the animal and/or the xenograft, or by detecting presence or level of a biomarker of interest in the body fluid (e.g. blood) of the animal.

Methods of Producing the Animal Models

Another aspect of the present disclosure relates to methods of producing an animal model for a human disease associated with a first mutation of a target gene, comprising: a) obtaining an immuno-deficient animal; and b) grafting the animal at a first site with a first human xenograft comprising the target gene comprising the first mutation, and at a second site with a second human xenograft comprising the target gene but lacking the first mutation, wherein the first human xenograft and second human xenograft are isogenic.

An immuno-deficient animal can be obtained either through genetic modification, for example, by introducing a DNA sequence into the animal such that to promote a deficiency in functionally active B/T lymphocytes or/and NK cells. Examples of genetically modified immuno-deficient animals are commercially available BALB/c nude mice, C57BL nude mice, NIH nude mice, nude rat, CBA/N mice, Beige mice, SCID mice, Beige/Nude, SCID Beige/SCID NOD mice and such like. Alternatively, an immuno-deficient animal can be obtained by biological or chemical immuno-suppress methods, include, without limitation, immuno-suppression by repeated treatment with irradiation, cyclosporine, anti-Asialo GM1 antibody, or other immuno-suppressive agents or treatments well known in the art.

The xenograft is a graft of tissue or cells taken from a donor which is a species different from the animal model, and grafted into the animal model. The xenograft can be grafted to the animal model using any suitable methods known in the art, for example, by grafting cells subcutaneously, intraperitoneally, or intravenously through injection; or alternatively, by implanting a fraction of tissue through surgery. In some embodiments, for example, the xenograft is a piece of diseased tissue taken through biopsy, which is washed in PBS for a few times and then homogenized and resuspended in saline or PBS and optionally mixed a small amount of matrigel before being injected under the skin of the animal's upper back or left/right flanks. In other embodiments, the xenograft are tumor cells or cancerous cells, which are cultured and collected before use, the cells are then resuspended in saline or PBS and optionally mixed a small amount of matrigel before being injected under the skin of the animal's upper back or left/right flanks or being injected via tail vein.

Once grafted with xenografts, the animal model is allowed to grow for a time sufficient to simulate the lesion of the human disease. For example, given enough time for disease development, animal models grafted with cancerous cells may develop in-situ or metastatic tumors which can then be used to evaluate the efficacy of a test agent on the disease.

Methods of Using the Animal Models

Another aspect of the present disclosure relates to methods of using the animal models provided herein.

In certain embodiments, the present disclosure provides methods of assessing effect of a test agent on a human disease associated with a first mutation of a target gene, comprising: obtaining an immuno-deficient animal; and grafting the animal at a first site with a first human xenograft comprising the target gene comprising the first mutation, and at a second site with a second human xenograft comprising the target gene but lacking the first mutation, wherein the first human xenograft and second human xenograft are isogenic.

The term "test agent" as used herein refers to any substance, molecule, element, compound, or a combination thereof used for treating the disease. The term "test agent" is intended to include both known therapeutic agents and potential therapeutic agents. A test agent can be in any form including, but not limited to, protein, polypeptide, polynucleotide, small organic/inorganic molecule and the like. A test agent can be a natural product, extracts of a natural product, a synthetic compound or a combination of two or more substances. In some embodiments, the test agent includes antisense compounds. In other embodiments, the test agent includes antibodies. In some embodiments, the test agent is an anti-cancer agent.

The term "anti-cancer agent" refers to any substance, compound or composition, when administered to a subject, has effect to inhibit, prevent or suppress cancer cell growth, proliferation or metastasis. In some embodiments, the "anti-cancer agent" may include any kind of agents that is currently known in the art or that will be identified in the future to be used for cancer therapy, including but not limited to kinase inhibitors (e.g. a c-MET inhibitor, an ALK inhibitor, a PDGFR inhibitor, a c-KIT inhibitor, and an EGFR inhibitor), anti-hormonal agents (e.g. steroid receptor antagonists, anti-estrogens, anti-androgens, agonists and/or antagonists of glycoprotein hormones such as follicle stimulating hormone (FSH), thyroid stimulating hormone (TSH), and luteinizing hormone (LH) and LHRH (leuteinizing hormone-releasing hormone), and antagonists for other nonpermissive receptors, such as antagonists for RAR, RXR, TR, VDR), anti-angiogenic agents (e.g. VEGFR inhibitors, VEGF inhibitors, integrin receptor antagonists and integrin antagonists, factors such as IFN-alpha; angiostatin and plasminogen fragments; endostatin; thrombospondin; platelet factor 4 (PF4); plasminogen activator/urokinase inhibitors; urokinase receptor antagonists; heparinases; fumagillin analogs; suramin and suramin analogs; angiostatic steroids; bFGF antagonists; flk-1 and flt-1 antagonists; anti-angiogenesis agents such as MMP-2 (matrix-metalloprotienase 2) inhibitors and MMP-9 (matrix-metalloprotienase 9) inhibitors), chemotherapy agents (e.g. alkylating agents or agents with an alkylating action, anti-metabolites, antibiotics, alkaloids, and other antitumor agents, such as paclitaxel and pactitaxel derivatives, the cytostatic agents, glucocorticoids and corticosteroids, nucleoside enzyme inhibitors such as hydroxyurea, amino acid depleting enzymes such as asparaginase, leucovorin, folinic acid, raltitrexed, and other folic acid derivatives, and similar, diverse antitumor agents) and the like.

In some embodiments, the anti-cancer agent is an EGFR inhibitor, eg. small molecules, antibodies, or RNA agents targeting EGFR, EGFR-related family members, or immediate effectors in the EGFR cascade including but not limited to Ras, Raf, and MEK1.

The method of assessing the effect of a test agent on a human disease comprises determining the effect of the test agent on the first and the second human xenografts. For example, when the human disease is cancer, the test agent is an active agent for cancer therapy, the effect of a test agent is evaluated by assessing the size and/or weight of the human xenografts, and/or assessing the morbidity and mortality of the animal, for example, at the time of routine monitoring, the physical conditions of the animals will be checked for any effects of tumor growth and any changes in normal behavior such as mobility, food and water consumption, body weight gain/loss, eye/hair matting etc. In some embodiments, blood and tissue samples (e.g. the xenograft) are collected for more in-depth assessment of the animal's health condition, parameters to be assessed may include but not limited to, immune system activity, tumor cells biomarkers, pro-inflammatory/anti-inflammatory factors, drug metabolisms, immune cells infiltration, malignancy level, metastasis condition and the like.

In certain embodiments, the present disclosure provides methods of profiling effects of a test agent on a human disease associated with different mutations of a target gene, comprising: obtaining a first animal model provided herein for the human disease associated with a first mutation of the target gene; administering the test agent to the first animal model; determining the effect of the test agent on the first and the second human xenografts respectively of the first animal model; obtaining a second animal model provided herein for the human disease associated with a second mutation of the target gene; administering the test agent to the second animal model; determining the effect of the test agent on the first and the second human xenografts respectively of the second animal model; and recording the effects of the test agent on the first animal model and the second animal model respectively. For example, when the target gene is K-RAS, the different mutations are selected from a group consisting of G12C, G12R, G12S, G12V, G12D, G12A, G13V/D; a first animal model grafted with a first xenograft of first mutation G12C of K-RAS and a second xenograft of wild type K-RAS (having a G12) is produced, an test agent for cancer therapy is then administered to the first animal, and the effect (eg. effect on tumor growth) of the test agent on the first xenograft and the second xenograft of the first animal is then determined and recorded; a second animal grafted with a first xenograft of first mutation G12R of K-RAS and a second xenograft of wild type K-RAS (having a G12) (alternatively, the second xenograft can be of a second mutation that is not the same as the first mutation on the same animal, eg. a G12S) is produced, an test agent for cancer therapy is then administered to the second animal model, and the effect (eg. effect on tumor growth) of the test agent on the first xenograft and the second xenograft of the second animal model is then also determined and recorded, by doing such, data regarding the effect of a test agent (or test agents) on different mutations will be collected and can be used for estimating a therapy on patients with specific gene mutations of a gene.

In certain embodiments, the present disclosure provides methods of identifying an active agent effective on a human disease associated with a first mutation of a target gene, comprising: a) obtaining the animal model provided herein for the human disease; b) administering a test agent to the animal model; c) determining the effect of the test agent on the first and the second human xenografts, respectively of the animal model; wherein therapeutic improvement in the first human xenograft indicates the test agent is an active agent. This method can be used to screen test agents to identify whether any test agent is active on the human disease. To be more specific, for example, a first animal model grafted with a first xenograft of first mutation G12C of K-RAS and a second xenograft of wild type K-RAS (having a G12) is produced, and used for identifying an active agent from a group of test agents, a first test agent from the group of the test agents is administered to the first animal model, the effect of the first test agent on the first and the second human xenografts of the first animal is then determined, if no therapeutic improvement is identified in the first human xenograft, then administer a second test agent to the first animal model, until an active agent for the first mutation is identified with a therapeutic improvement in the first xenograft.

In certain embodiments, the present disclosure provides methods of predicting effect of a test agent on a individual having a disease associated with a first mutation of a target gene, comprising: (a) obtaining the animal model provided herein for the disease, wherein the first human xenograft and the second human xenograft are both derived from the individual except that one of the xenografts has been treated to either introduce or remove the first mutation, such that the first xenograft comprises the target mutation and the second human xenograft lacks the target mutation, and the first xenograft and second xenograft are isogenic; (b) administering the test agent to the animal model; and (c) determining the effect of the test agent on the first and the second human xenografts, respectively of the animal model, wherein therapeutic improvement in the first human xenograft indicates efficacy of the test agent.

The term "therapeutic improvement" as used herein refers to a positive outcome of the treatment on the animal model, wherein the animal, or specifically the human xenograft in the animal, demonstrates a reduction in severity, in size, or in a disease-related biomarker, or an improvement in conditions associated with the disease or disorder. In some embodiment, therapeutic improvement refers to an inhibition of tumor growth, progression or metastasis in the animal. In some embodiment, therapeutic improvement refers to a lower morbidity and/or mortality, and/or a longer survival time of the animal.

As used herein, the term "subject" or "individual" or "patient" used interchangeably here refers to a human suffered from a disease, disorder or conditions related to a disease or disorder. In some embodiments, a subject refers to a human suffers from cancer. In some embodiments, the term refers to a human in need of treatment for cancer with an anti-cancer agent. In some embodiments, the term refers to a human in need of treatment for cancer with an EGFR inhibitor. In some embodiments, the term refers to a human bearing a mutation of K-RAS; and in some cases said human bearing the mutation has being treated with an EGFR inhibitor and demonstrates resistance to the EGFR inhibitor.

Unless defined otherwise, all technical and scientific terms used herein have the same meaning as commonly understood by one of ordinary skill in the art to which this invention belongs.

As used herein, the singular forms "a", "an" and "the" are intended to include the plural forms as well, unless the context clearly indicates otherwise. It will be further understood that the terms "comprises", "comprising", "includes" and/or "including," if used herein, specify the presence of stated features, steps, operations, elements and/or components, but do not preclude the presence or addition of one or more other features, steps, operations, elements, components and/or groups thereof. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "3000 mm$^2$" is intended to mean "about 3000 mm$^2$". As used herein, the term "about," when used in reference to a particular recited numerical value, means that the value may vary from the recited value by no more than 1%.

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

Although any methods and materials similar or equivalent to those described herein can be used in the practice or testing of the present disclosure, preferred methods and materials are now described.

The following examples are presented to illustrate the present disclosure. They are not intended to limiting in any manner. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Production of Animal Models with Isogenic Dual-Xenograft

In this example, isogenic dual-xenograft animal model for a human disease was produced with isogenic pairs of colorectal cell lines, wherein each pair contained one wild-type K-RAS cell line and one mutated K-RAS (selected from a group consisting of G12C, G12R, G12S, G12V, G12D, G12A, G13V/D) cell line. Said pair of isogenic colorectal cell lines were grafted respectively to left and right flanks of the same mouse.

Cell Culture:

The SW48 series colorectal adenocarcinoma cells were obtained from Horizon Discovery Ltd (see below in Table 1 for Catalogue number details), and maintained in vitro as a monolayer culture in McCoy's 5A medium supplemented with 10% heat inactivated fetal bovine serum, 2 mM L-glutamine, with or without G418, at 37° C. in an atmosphere of 5% $CO_2$ in air. The tumor cells were routinely subcultured every 3-5 days by trypsin-EDTA treatment. Cells growing in an exponential growth phase were harvested and counted for tumor inoculation. HD 103-002 cell line was derived from parental SW48 cell line HD PAR-006 with heterozygous knock-in of KRAS activating mutation-G13D; HD 103-007 cell line was derived from parental SW48 cell line HD PAR-006 with heterozygous knock-in of KRAS activating mutation-G12V.

TABLE 1

Cell lines used in producing the isogenic dual-xenograft animal model

| Cell lines | Catalogue number | Genotype | Parental cell line |
|---|---|---|---|
| SW48 | HD PAR-006 | KRAS WT | HD PAR-006 |
|  | HD 103-002 | KRAS (G13D/+) | HD PAR-006 |
|  | HD 103-007 | KRAS (G12V/+) | HD PAR-006 |

Animals:

Nude mice purchased from HFK are used for the study, which are all males, 10 weeks old, weighing approximately 18-22 g. A total number of 30 mice are needed for each experiment.

Tumor Grafting:

Each mouse is grafted subcutaneously at the left and right flank with SW48 tumor cells ($1\times10^7$ cells) in 0.1 ml of PBS for tumor development, among which 15 mouse are grafted with $1\times10^7$HD PAR-006 cells at their left flank and with $1\times10^7$ HD 103-002 cells at their right flank, and the other 15 mouse are grafted with $1\times10^7$ HD PAR-006 cells at their left flank and with $1\times10^7$ HD103-007 cells at their right flank. Mice with xenografts are then allow sufficient time (in present embodiment, around 5-8 days) to develop solid tumor. After inoculation, the animals will be checked daily for tumor growth, and treatments with test agents will generally start when the mean tumor volume is 100~200 mm$^3$.

Example 2: Use of the Isogenic Dual-Xenograft Animal Model in New Drug Screening and Selection of Indications Isogenic dual-xenograft mice produced in accordance to the methods described in Example 1 were used to evaluate test agents for their efficacy on the disease associated with mutations of gene. More specifically, mice with different KRAS mutations were treated with EGFR inhibitors to address the question of resistant phenotypes elicited by different KRAS mutations. This design allows direct comparison of wild type and mutant isogenic pairs for treatment responses that are associated with the defined genetic variations.

TABLE 2

Groups and Treatments

| Group | Animal No. | Location | Tumor | Cell No. | Treatment |
|---|---|---|---|---|---|
| 1 | 15 | Left flank | SW48-parental HD PAR-006: SW48 (SNB: 276) | $1 \times 10^7$ | Vehicle (5 mice) Cetuximab |
|  |  | Right flank | HD 103-002: SW48 KRAS (G13D/+) (SNB: 25) | $1 \times 10^7$ | (5 mice), Erlotinib (5 mice) |
| 2 | 15 | Left flank | SW48-parental HD PAR-006: SW48 (SNB: 276) | $1 \times 10^7$ | Vehicle (5 mice) Cetuximab |
|  |  | Right flank | HD 103-007: SW48 KRAS (G12V/+) (SNB: 53) | $1 \times 10^7$ | (5 mice), Erlotinib (5 mice) |

TABLE 3

Treatments Regimen

| Treatment | Dose (mg/kg) | Dosing Route | Schedule |
|---|---|---|---|
| Vehicle(saline) | — | — | — |
| Cetuximab | 0.5 mg/mouse/ treatment | i.p. | Twice per week, 2 wks |
| Erlotinib | 50 mg/kg | p.o. | Once daily, 14 days |

Observations:

After inoculation, the animals were checked daily for morbidity and mortality. At the time of routine monitoring, the animals were checked for any effects of tumor growth and treatments on normal behavior such as mobility, visual estimation of food and water consumption, body weight gain/loss (body weights will be measured twice weekly), eye/hair matting and any other abnormal effect. Death and observed clinical signs were recorded on the basis of the numbers of animals within each subset.

Data Collecting Endpoints:

The major endpoint was to evaluate the tumor growth. Tumor sizes were measured twice weekly in two dimensions using a caliper, and the volume were expressed in mm3 using the formula: V=0.5 a×b$^2$, where a and b are the long and short diameters of the tumor, respectively.

Termination:

Animals that were observed to be in a continuing deteriorating condition or for which the tumor size exceeds 3000 mm$^3$ (or for which the mean tumor size of the group exceeds 2000 mm$^3$) were euthanized prior to death, or before reaching a comatose state. Animals showing obvious signs of severe distress and/or pain should be humanely sacrificed. In case of following situations, the animals were euthanized: 1) Animals have lost significant body mass (emaciated). Obvious body weight loss >20%; and 2) Animals can not get to adequate food or water.

Figure 1B:
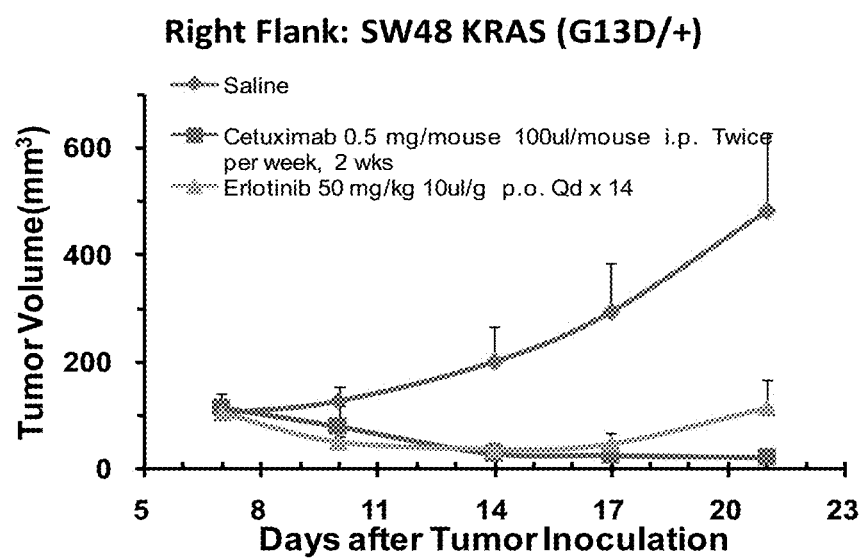
FIG. 1B. Antitumor activity of Control agent (Saline), Cetuximab, and Erlotinib (n=5/group) in the treatment of SW48-parental and SW48-KRAS (G13D/+) Isogenic Dual Xeno models. The data show the tumor volume of SW48-KRAS (G13D/+) xenograft in the models. Each data point represents an average of data from 5 individual mice, error bars represent SEM.
Figure 1C:
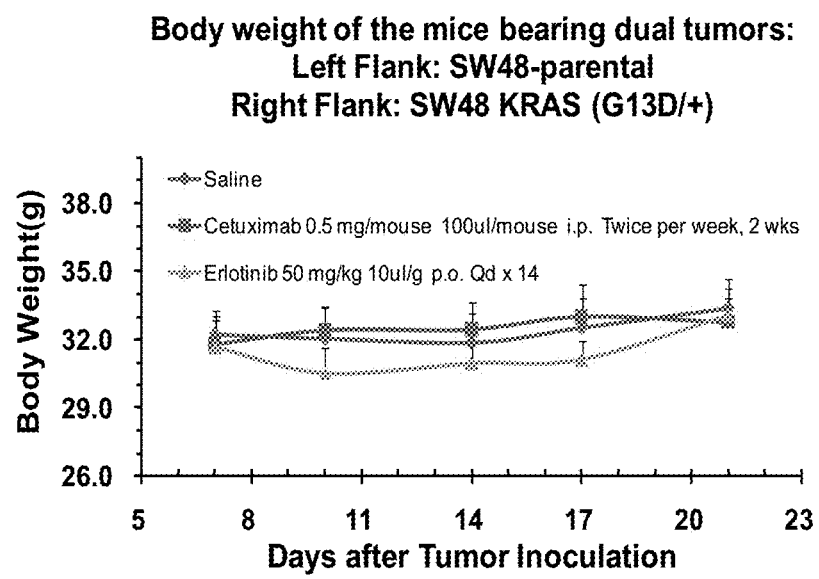
FIG. 1C. The body weight changes of the mice bearing dual xenografts (left flank: SW48-parental; right flank: SW48-KRAS (G13D/+)). (Each data point represents an average of data from 5 individual mice, error bars represent SEM.
Figure 2A:
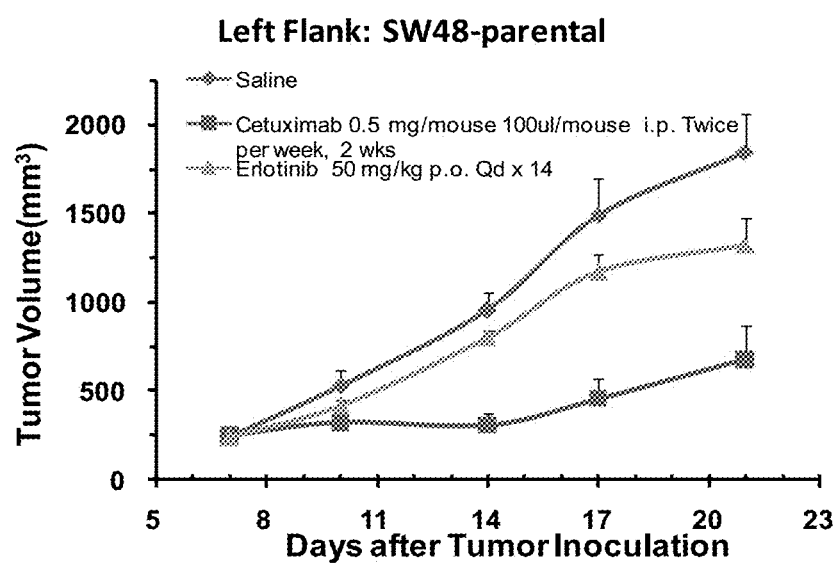
FIG. 2A. Antitumor activity of Control agent (Saline), Cetuximab, and Erlotinib (n=5/group) in the treatment of SW48-parental and SW48-KRAS (G12V/+) Isogenic Dual Xeno models. The data show the tumor volume of SW48-parental xenograft in the models. Each data point represents an average of data from 5 individual mice, error bars represent SEM.
Figure 2B:
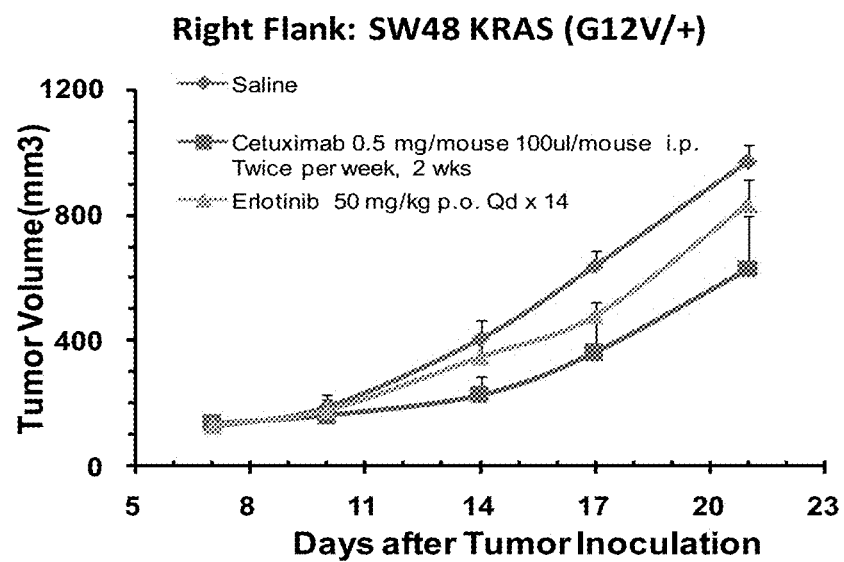
FIG. 2B. Antitumor activity of Control agent (Saline), Cetuximab, and Erlotinib (n=5/group) in the treatment of SW48-parental and SW48-KRAS (G12V/+) Isogenic Dual Xeno models. The data show the tumor volume of SW48-KRAS (G12V/+) xenograft. Each data point represents an average of data from 5 individual mice, error bars represent SEM.
Figure 2C:
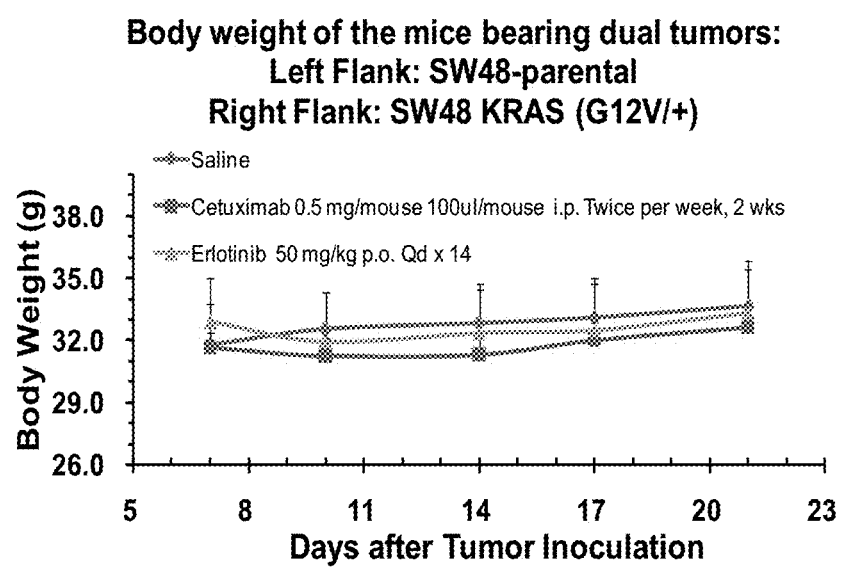
FIG. 2C. The body weight changes of the mice bearing dual xenografts (left flank: SW48-parental; right flank: SW48-KRAS (G12V/+)). Each data point represents an average of data from 5 individual mice, error bars represent SEM.

The study results in the isogenic animal models were shown in FIG. 1 and FIG. 2. As shown in FIG. 1, Cetuximab and Erlotinib both significantly reduced the tumor volume of the SW48-parental xenograft in the animal models (FIG. 1A), and also significantly reduced the tumor volume of the SW48-KRAS (G13D/+) xenograft (FIG. 1B). The body weight changes of the mice bearing dual isogenic xenografts were comparable in the saline group and the treatment group (FIG. 1C). As shown in FIG. 2, Cetuximab and Erlotinib both reduced the tumor volume of the SW48-parental xenograft in the animal models (FIG. 2A), but the reduction on the tumor volume of the SW48-KRAS (G12V/+) xenograft were not as significant as on the SW48-KRAS-parental xenograft (FIG. 2B). The body weight changes of the mice bearing dual isogenic xenografts were comparable in the saline group and the treatment group (FIG. 2C).

The antitumor activities on Tumor Volume of Erlotinib in the Treatment of SW48-parental, SW48 KRAS (G13D/+) and SW48 KRAS (G12V/+) Isogenic DualXeno models were summarized below in Table 4. Table 5 summarized antitumor activities on Tumor Volume of Cetuximab in the Treatment of SW48-parental, SW48 KRAS (G13D/+) and SW48 KRAS (G12V/+) Isogenic DualXeno models.

TABLE 4

Antitumor Activity on Tumor Volume of Erlotinib in the Treatment of SW48-parental, SW48 KRAS (G13D/+) and SW48 KRAS (G12V/+) Isogenic DualXeno models

| Erlotinib Treatment (50 mg/kg, p.o., Qd x 14) | T/C on Day 21 | TGI on Day 21 |
|---|---|---|
| SW48 parental line | 59%~72% | 28%~41% |
| SW48 KRAS(G13D/+) | 24% | 76% |
| SW48 KRAS(G12V/+) | 86% | 14% |

TABLE 5

Antitumor Activity on Tumor Volume of Cetuximab in the Treatment of SW48-parental, SW48 KRAS (G13D/+) and SW48 KRAS (G12V/+) Isogenic DualXeno models

| Cetuximab Treatment (0.5 mg/mouse, i.p. BIW x 2 wks) | T/C on Day21 | TGI on Day21 |
|---|---|---|
| SW48 parental line | 30%~37% | 63%~70% |
| SW48 KRAS(G13D/+) | 4% | 96% |
| SW48 KRAS(G12V/+) | 65% | 35% |

The result in FIG. 1 and Table 4 and 5, indicated that the SW48 KRAS (G12V/+) is resistant to Erlotinib and Cetuximab compared to the parental line: in the SW48 parental line, Erlotinib treatment resulted in TGI=28~41%, and Cetuximab treatment resulted in TGI=63~70%; in SW48 KRAS (G12V/+), Erlotinib treatment resulted in TGI=14%, and Cetuximab treatment resulted in TGI=35%. The result in FIG. 2 and Table 5, indicated that the SW48 KRAS (G13D/+) remains sensitive to Erlotinib and Cetuximab compared to the parental line: in the SW48 parental line, Erlotinib treatment resulted in TGI=28~41%, and Cetuximab treatment resulted in TGI=63~70%; in SW48 KRAS (G13D/+), Erlotinib treatment resulted in TGI=76%, and Cetuximab treatment resulted in TGI=96%.

Our data support the clinical finding (Wendy De Roock, et al. JAMA 2010, 304 (16), pp 1812) that KRAS mutation G13D is quite different from other KRAS mutations, and cells carrying the mutation can remain sensitive to EGFR targeting agents such as Cetuximab and Erlotinib. Therefore, proved that our in vivo isogenic dual-xenograft animal models harboring KRAS mutations are useful tools for screening of next generation agents targeting resistance mechanisms.

While the invention has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. An immuno-deficient non-human animal useful as an animal model for cancer comprising
    (a) a first human xenograft comprising a mutation in K-RAS gene; and
    (b) a second human xenograft that is wild-type in the K-RAS gene,
    wherein the mutation is K-RAS G12V or K-RAS G13D, and wherein the first human xenograft and the second human xenograft are isogenic.

2. The non-human animal of claim 1, wherein the first human xenograft and the second human xenograft are grafted to different sites of the animal.

3. The non-human animal of claim 1, wherein the first human xenograft and the second human xenograft are grafted to the same site of the animal.

4. The non-human animal of claim 1, wherein the first human xenograft is heterozygous in the K-RAS gene.

5. The non-human animal of claim 1, wherein the first human xenograft is labeled with a first reporter and the second human xenograft is labeled with a second reporter.

6. The non-human animal of claim 1, wherein the animal is a mammal.

7. The non-human animal of claim 6, wherein the mammal is a rodent.

8. The non-human animal of claim 7, wherein the rodent is a mouse, a rat, a guinea pig, or a hamster.

9. The non-human animal of claim 1, wherein the cancer is colorectal cancer.

10. The non-human animal of claim 5, wherein the first and second reporter are green fluorescent protein and red fluorescent protein, respectively, or vice versa.

* * * * *